(12) United States Patent
Beiswenger et al.

(10) Patent No.: US 8,801,609 B2
(45) Date of Patent: Aug. 12, 2014

(54) APPARATUS AND SYSTEM FOR PREDICTIVE HEALTH MONITORING

(75) Inventors: John L. Beiswenger, Strasburg, PA (US); Jody L. Taualofai, Lancaster, PA (US)

(73) Assignee: Predictive, Inc., Strasburg, PA (US)

( * ) Notice: Subject to any disclaimer, the term of this patent is extended or adjusted under 35 U.S.C. 154(b) by 987 days.

(21) Appl. No.: 10/599,344

(22) PCT Filed: Mar. 24, 2005

(86) PCT No.: PCT/US2005/010041
§ 371 (c)(1),
(2), (4) Date: Sep. 26, 2006

(87) PCT Pub. No.: WO2005/096920
PCT Pub. Date: Oct. 20, 2005

(65) Prior Publication Data
US 2008/0306352 A1    Dec. 11, 2008

Related U.S. Application Data

(60) Provisional application No. 60/556,708, filed on Mar. 26, 2004.

(51) Int. Cl.
| A61B 5/00 | (2006.01) |
| A61B 5/09 | (2006.01) |
| A61B 10/00 | (2006.01) |
| A61B 5/01 | (2006.01) |

(52) U.S. Cl.
CPC ............... *A61B 5/09* (2013.01); *A61B 10/0051* (2013.01); *A61B 5/01* (2013.01)
USPC .......................................... 600/301; 600/529

(58) Field of Classification Search
USPC ................... 600/300–301, 529–531; 433/215
See application file for complete search history.

(56) References Cited

U.S. PATENT DOCUMENTS

| 4,294,262 | A | * | 10/1981 | Williams et al. | ............... | 600/539 |
| 5,549,117 | A | * | 8/1996 | Tacklind et al. | ............... | 600/529 |
| 5,816,246 | A | * | 10/1998 | Mirza | ........................... | 600/539 |
| 5,922,610 | A | * | 7/1999 | Alving et al. | ................. | 436/116 |
| 6,314,822 | B1 | * | 11/2001 | Ford | ........................... | 73/861.77 |

(Continued)

FOREIGN PATENT DOCUMENTS

JP     2004041472 A     2/2004

OTHER PUBLICATIONS

Written Opinion of the International Searching Authority, International Application No. PCT/US 2005/010041, dated Jun. 29, 2005, 6 pages.

*Primary Examiner* — Gary Jackson
*Assistant Examiner* — Bobby Soriano
(74) *Attorney, Agent, or Firm* — Barley Snyder

(57) ABSTRACT

An apparatus and system are provided for monitoring an individual, a group or a community of individuals for respiratory infections. Predictive health data, such as waking peak expiratory flow rate ("WPF") and basal metabolic temperature ("BMT") are measured and charted to provide an indication of early stage respiratory infection. Data may be collected for target populations and reported to health agencies for use in combating the spread of infection. An apparatus is provided which can simultaneously measure WPF and BMT and other health-condition-related values and automatically transmit readings to a data collection and analysis program on a remote computer.

13 Claims, 4 Drawing Sheets

(56) References Cited

U.S. PATENT DOCUMENTS

| | | |
|---|---|---|
| 6,468,222 B1* | 10/2002 | Mault et al. .................... 600/531 |
| 6,733,464 B2 | 5/2004 | Olbrich et al. |
| 6,838,993 B2 | 1/2005 | Beiswenger et al. |
| 6,958,691 B1 | 10/2005 | Anderson et al. |
| 7,108,659 B2* | 9/2006 | Ross et al. .................... 600/529 |
| 2002/0061495 A1* | 5/2002 | Mault ........................... 433/215 |
| 2002/0087057 A1* | 7/2002 | Lovejoy et al. ................ 600/349 |
| 2003/0159697 A1* | 8/2003 | Wallace ..................... 128/204.26 |
| 2003/0216659 A1* | 11/2003 | Brawner et al. ............... 600/532 |
| 2004/0186390 A1* | 9/2004 | Ross et al. .................... 600/532 |
| 2005/0094707 A1* | 5/2005 | Lee et al. ...................... 374/163 |
| 2005/0096558 A1* | 5/2005 | Friedman et al. ............. 600/532 |
| 2008/0053194 A1* | 3/2008 | Ahmad ....................... 73/25.01 |

* cited by examiner

| County | Population | | Sentries | | | Reporting | | | |
|---|---|---|---|---|---|---|---|---|---|
| Lackawana | 213,295 | 1.7% | 3,199 | 1.5% | | 2,847 | 89.0% | | |
| | 2,164 | 76.00% | 256 | 9.01% | 114 | 4.00% | 29 | 1.00% | 14 | .50% |
| | 142 | 5.00% | 97 | 3.40% | 28 | 1.00% | 1 | .03% | 1 | .03% |
| | 1 | .03% | 0 | .00% | 0 | .00% | 0 | .00% | 0 | .00% |
| Lancaster | 470,658 | 3.8% | 7,060 | 1.5% | | 6,425 | 91.0% | | |
| | 5,012 | 78.00% | 579 | 9.01% | 254 | 3.96% | 84 | 1.30% | 0 | .00% |
| | 257 | 4.00% | 193 | 3.00% | 45 | .70% | 0 | .00% | 0 | .00% |
| | 1 | .02% | 0 | .00% | 0 | .00% | 0 | .00% | 0 | .00% |
| Lawrence | 94,643 | 0.7% | 1,420 | 1.5% | | 1,250 | 88.0% | | |
| | 873 | 70.00% | 75 | 6.00% | 63 | 5.00% | 25 | 2.00% | 19 | 1.50% |
| | 50 | 4.00% | 55 | 4.40% | 25 | 2.00% | 13 | 1.04% | 25 | 2.00% |
| | 2 | .16% | 0 | .00% | 1 | .01% | 12 | 1.00% | 12 | 1.00% |
| Lebanon | 120,327 | 1.0% | 1,805 | 1.5% | | 1,660 | 92.0% | | |
| | 1,311 | 79.00% | 167 | 10.06% | 33 | 2.00% | 16 | 1.00% | 8 | .48% |
| | 100 | 6.00% | 23 | 1.40% | 2 | .12% | 0 | .00% | 0 | .00% |
| | 0 | .00% | 0 | .00% | 0 | .00% | 0 | .00% | 0 | .00% |
| Lehigh | 312,090 | 2.5% | 4,681 | 1.5% | | 4,072 | 87.0% | | |
| | 2,972 | 73.00% | 123 | 3.02% | 163 | 4.00% | 122 | 3.00% | 61 | 1.50% |
| | 244 | 6.00% | 121 | 2.98% | 81 | 1.99% | 20 | .49% | 21 | .52% |
| | 81 | 2.00% | 41 | 1.01% | 19 | .47% | 1 | .02% | 2 | .05% |
| End of Report | 12,281,000 | 100.00% | 184,215 | 1.5% | | 165,794 | 90.0% | | |

FIG. 3

APPARATUS AND SYSTEM FOR PREDICTIVE HEALTH MONITORING

FIELD OF THE INVENTION

The present invention is related to health monitoring, and more particularly to an apparatus and system for monitoring individuals and/or populations to predict impending changes in respiratory health and provide alerts to those changes.

BACKGROUND OF THE INVENTION

Many individuals are susceptible to respiratory infections including bronchitis and pneumonia. In the United States alone, ordinary pneumonia killed 62 thousand people in 1999. Asthmatics are particularly susceptible to respiratory infections. 17 million people are known to have asthma in the United States.

Infectious disease is the third leading cause of death in the United States. Moreover, deaths from infectious disease have been increasing. More Americans died per thousand due to infectious disease in 2000 than in 1980. 90,000 people die each year in the United States due to nosocomial infections, many resulting from surgery. Individuals whose immune systems are compromised are particularly susceptible.

Peak flow meters are recommended to monitor the lung function value of asthmatic's airways. This inexpensive device provides a non-invasive, inexpensive, convenient means to monitor lung function values and can be used at home by asthmatics of all ages. Peak flow meter readings fall before symptoms of asthma are otherwise noticed (providing early detection).

Body temperatures of 37.8° C. (100° F.) or above, are classified as a fever. Fevers are described as low-grade [37.8° C. (100° F.) to 38.9° C. (102° F.)] or high-grade [above 39.5° C. (103° F.)]. When an infection first occurs, the immune system causes white blood cells to move to the site of the localized infection to fight the infection and the core body temperature of the individual begins to rise. As an infection spreads to other areas of an organ or other areas of the body and the number of white blood cells involved in fighting the infection increases, causing a proportional increase in the body's core temperature. A spreading infection neither suddenly invades all susceptible tissues in the body nor immediately involves all white blood cells. An infection spreads over a period of time—different for different diseases and pathways.

Primary Prevention (i.e., taking steps to prevent the occurrence of an infection) is, of course, important. However, because of travel, meetings, conventions, and the many other ways individuals come into contact with large numbers of people, infections still occur.

Secondary Prevention is the early detection of an infection followed by actions taken immediately to reverse, halt or retard its progression (e.g., taking antiviral drugs, anti-oxidants or antibiotics). Secondary Prevention can be very effective in protecting individuals from the adverse effects of infectious disease, but most therapeutic treatments are not optimally effective if they are not started during the early stages of an infectious disease. Furthermore, detecting infections in their very early stages has been difficult due to the fact that physical symptoms are often not yet apparent.

Accordingly, a need exists for an effective means for detecting and reporting impending respiratory infections.

SUMMARY OF THE INVENTION

An apparatus and system are provided for monitoring an individual, a group, or a community of individuals for respiratory infections. Predictive health data, such as waking peak expiratory flow (WPF) and basal metabolic temperature (BMT) are measured, charted and correlated to provide an indication of early stage respiratory infection in an individual. Data may be collected for target populations and reported to health agencies for use in combating the spread of infection in an effected target population. An apparatus is provided which can simultaneously measure WPF and BMT and automatically transmit readings to a data collection and analysis program on a remote computer. The system can further provide automatic reporting to individuals, their doctors, and/or health agencies.

BRIEF DESCRIPTION OF THE DRAWINGS

Exemplary embodiments of the invention will be described with reference to the accompanying drawings, of which:

FIG. 3 shows a health agency report for monitoring respiratory infections in populations according to an exemplary embodiment of the invention.

DETAILED DESCRIPTION OF THE INVENTION

Figure 1:
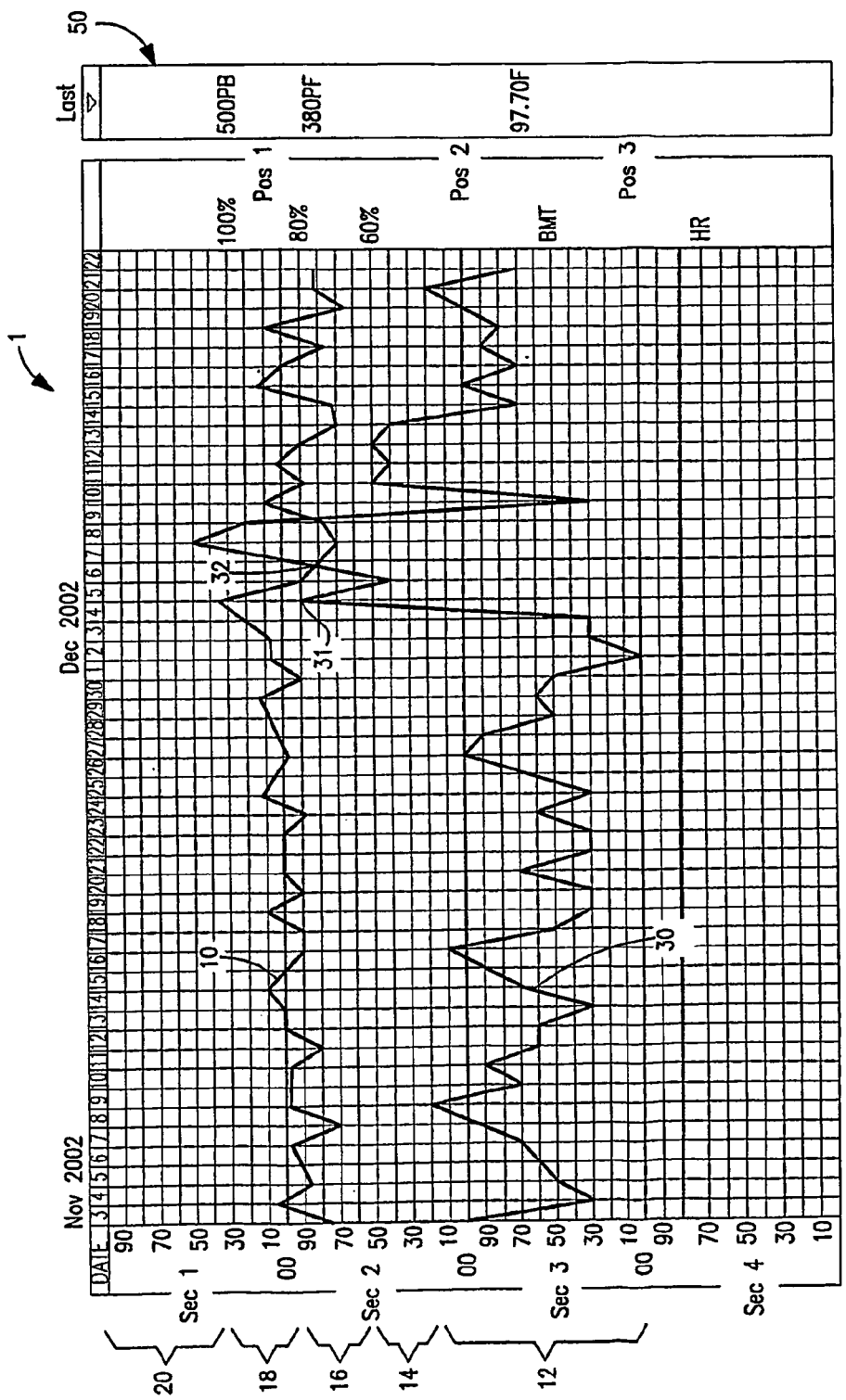
FIG. 1 shows a predictive health monitoring chart for identifying early stage respiratory infections in an individual according to an exemplary embodiment of the invention.

The present invention provides an apparatus and system for monitoring individuals and/or populations to predict impending changes in respiratory health and provide alerts and/or reports of those changes. The inventors have determined that respiratory infections can be detected by changes in BMT before other symptoms become discernable. An abnormal elevation in BMT is a near-universal and early indication of infection. It is a precursor to symptoms, thus leading infection symptoms and speeding intervention. Early detection of a respiratory infection permits an earlier response, which typically results in a better outcome. Not all changes in BMT, however, indicate respiratory infection, as cyclical physiological changes, stimulated by certain hormones released into the blood stream, increase and decrease basal metabolism which results in a BMT that cycles up and down.

Basal metabolism is the level of metabolism needed for maintenance of life when an individual is at digestive, physical and emotional rest, such as just before an individual rises in the morning. An elevated basal metabolism indicates that an infection may be present. BMT can be measured immediately upon waking after 6 to 8 hours of sleep. Normal daytime body temperatures range from 98.6 to 100° F., depending on the level and type of activity. However, normal basal temperatures range from 97.0 to 98.6° F. Physiological changes, stimulated by certain hormones released into the blood stream by endocrine glands, increase the body's basal metabolic rate (BMR), which results in an increase in BMT. Other hormones regulate the stimulating hormones and effectively reduce BMR and therefore BMT. A cyclical BMT results, making accurate analysis of raw values difficult unless properly scaled graphing is employed such as described in the following section.

Predictive Charting Template

According to an exemplary embodiment of the present invention, Predictive Chart 1 is used to plot a BMT curve 10, rendering abnormal elevations of BMT, and therefore early infections, readily identifiable. The Predictive Chart 1 comprises a grid of squares comprising rows extending in the horizontal and columns extending in the vertical direction. The squares are divided into five vertically adjacent horizontal bands, 12, 14, 16, 18, 20. The BMT curve 10 is plotted on the predictive chart 1, with the columns corresponding to temporal increments along a horizontal direction, such as, for example, one square for each day. In the vertical direction, the rows correspond to temperature increments, for example one tenth of one degree Fahrenheit (0.1° F.) for each square or row. BMT is tracked on Predictive Chart 1 by entering a BMT reading for each day, so that cyclical fluctuations and trends can be readily viewed along the horizontal direction of Predictive Chart 1. The bands represent normal and elevated ranges for BMT. The first band 12 extends for twelve vertically adjacent rows corresponding to temperatures from 96.9° F. to 98.1° F. and represents the normal range for the BMT of a male. The second band 14, located directly above the first band 12, extends for four vertically adjacent rows corresponding to temperatures from 98.1° F. to 98.5° F. and represents a first elevated range for BMT, still normal for a female's BMT during the luteal phase of her reproductive cycle. A BMT in the second band 14 does not provide an accurate indication of infection for females, because BMT in band 14 is common during physiological changes, such as menstruation, but it does for males. The third band 16, located directly above the second band 14, extends for four vertically adjacent rows corresponding to temperatures from 98.5° F. to 98.9° F. and represents a second elevated range for BMT. This second elevated range for BMT generally indicates an abnormal elevation, and BMT 10 in the third band 16 is an indication of the early stages of an infection. The fourth band 18 extends for four vertically adjacent rows corresponding to temperatures from 98.9° F. to 99.3° F., and the fifth band 20 extends upward from 99.3° F. The fourth and fifth bands 18, 20 of Predictive Chart 1 represent additional elevated ranges for BMT and are also indicative of early stages of an infection.

In an exemplary embodiment of the invention, the horizontal bands 12, 14, 16, 18, 20 are color coded, for example, the first band 12 being pastel blue, the second band 14 being pastel pink, the third band 16 being yellow, the fourth band 18 being pastel green and the fifth band 20 being gray. The color coding enables healthcare workers, patients, and others to easily and accurately determine which band a particular BMT reading falls within, and thus determine whether that particular BMT reading is in the second, third, or fourth elevated ranges of the third 16 fourth 18 and fifth 20 bands, respectively, indicating early stage infection. As shown in FIG. 1, a BMT reading 31 of 98.9° F. was recorded for Dec. 5, 2002, which is plotted in the third band 16, indicating the early stages of an infection.

In an exemplary embodiment of the invention, a waking peak flow (WPF) curve 30 is also plotted on Predictive Chart 1. The normal range for waking peak flow, 80% to 100% of Peak Best (the best flow rate produced by the individual), is arranged to correspond to the fourth band 18, with daily WPF measurements plotted for each day and each vertically adjacent row of squares corresponding to a 5% increment in WPF measurements. As shown in FIG. 1, the third band 16 corresponds to abnormally low WPF readings of from 60% to 80%, indicative of a depressed respiratory condition. By correlating BMT and WPF, a particularly accurate indicator of a respiratory infection is provided which may be observed up to days before physical symptoms are experienced. When BMT rises into a band corresponding to abnormally high BMT (here the third, fourth, and fifth bands 16, 18, 20, respectively) and WPF readings simultaneously fall in a band corresponding to abnormally low WPF (here, also the third band 16), it is a strong indication of a respiratory infection. This indication typically occurs before other symptoms of respiratory infection are present, such as: fever, headache, tiredness [can be extreme], dry cough, sore throat, nasal congestion, body aches, etc. A physician can test to determine if the individual being monitored has the flu or there is some other causal factor. As shown in FIG. 1, on Dec. 7, 2002, the WPF curve 10 dropped into the third band 16 while the BMT curve 30 rose into the fourth band 18. Moreover, due to the arrangement of Predictive Chart 1, the BMT curve 30 and the WPF curve 10 cross each other at point 32 (during Dec. 6, 2002), providing a strong and easily recognizable indication of a respiratory infection.

In an ideal embodiment of the invention, waking heart rate (WHR), waking saliva acidity (WPh) and waking blood oxygen (WO2) curves are also plotted on Predictive Chart 1, because they too indicate the general health condition of the person being monitored.

Optionally, a last reading window 50 may be provided for presenting the most recent measurements in numerical form. In FIG. 1 for example, the most recent BMT reading of 97.7° F. and the most recent peak flow reading of 380 PF (peak-flow) are presented. These numerical values help healthcare workers to quickly evaluate the health of the person being monitored.

Predictive Health Monitoring Data Collection and Reporting System

Figure 2:
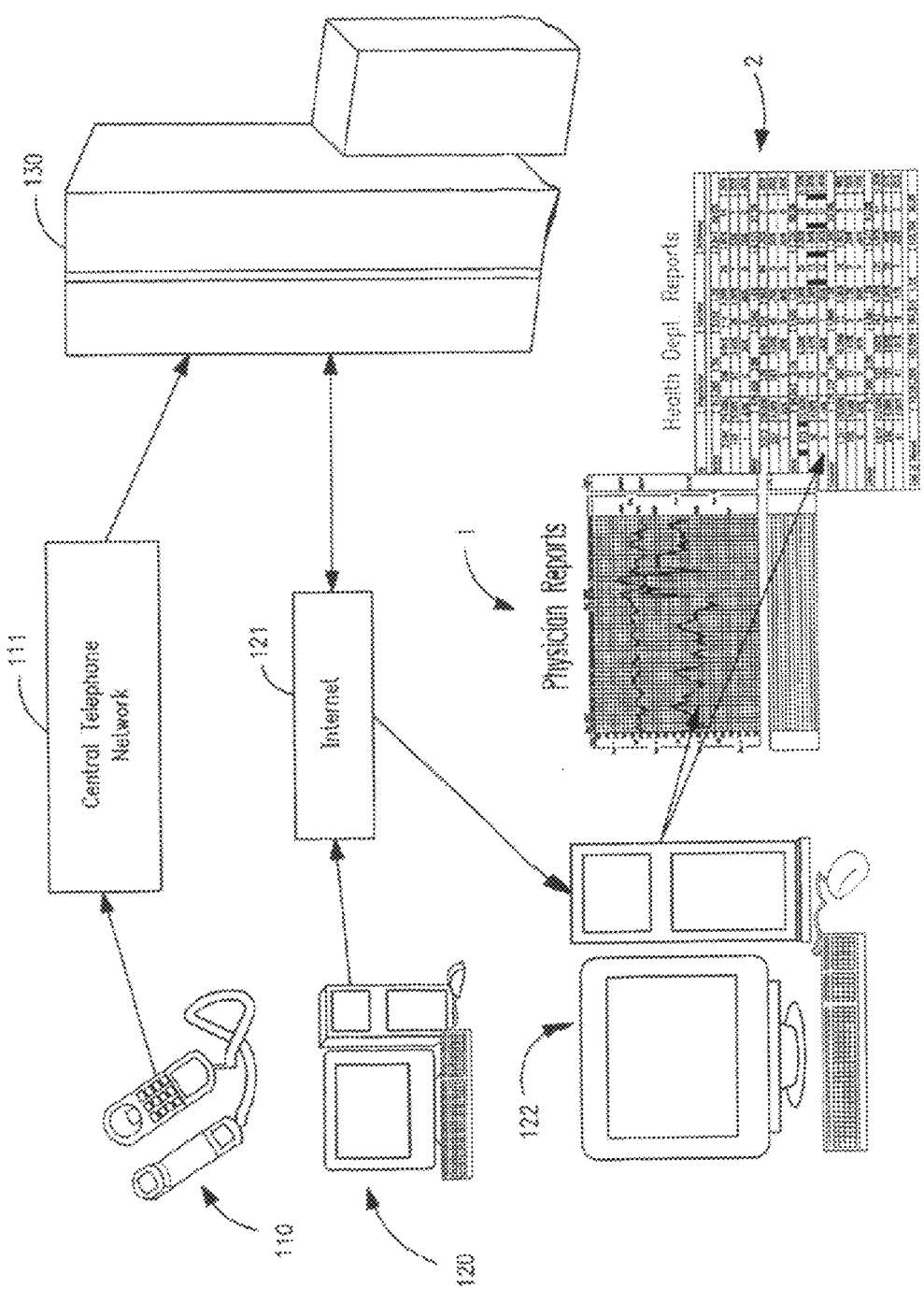
FIG. 2 shows a system for collecting, transmitting, and reporting predictive health monitoring data according to an exemplary embodiment of the invention.

According to an exemplary embodiment of the present invention, a system is provided for recording, transmitting (i.e., forwarding to a remote computer system), storing and reporting predictive health monitoring data to facilitate secondary prevention (i.e., the early detection and treatment) of respiratory infections, such as influenza, bronchitis, pneumonia, and SARS). As shown in FIG. 2, actual health monitoring data (in the present embodiment, BMT and WPF readings) are entered into a telephone 110 or a personal computer 120 and transmitted to a data collection and analysis program on a health monitoring computer 130 through a central telephone network 111 or the Internet 121, respectively. The data collection and analysis program on the health monitoring computer 130 then uses the health monitoring data to create a chart 1, which can be accessed by the individual being monitored or that individual's personal physician or others, so that indications of early stage respiratory infections can be identified and secondary prevention can be initiated. The monitored individual or physician may, for example, access the chart 1 through the Internet 121 on a personal computer 122.

The data collected by the data collection and analysis program on the health monitoring computer 130 can be protected by password or other means known in the art to maintain confidentiality of individual medical records in compliance with HIPAA.

Health Agency Report

As shown in FIG. 2, a health agency report 2 may also be created by the data collection and analysis program on the health monitoring computer 130, and accessed on a personal computer 122 by health agency representatives. This health agency report 2 can be used by health agency personnel to track the spread of respiratory infections and to facilitate remedial actions, such as broadcast alerts and screening, as well as allocation of anti-viral or antibiotic medications.

An exemplary embodiment of the health agency report 2 is shown in FIG. 3. In this exemplary embodiment, predictive health monitoring data is collected throughout the Commonwealth of Pennsylvania, and presented by county. Referring, for example, to Lawrence County, the population of Lawrence County is provided as a raw number (94,643) and as a percentage of the total population of Pennsylvania (0.7%). The number of sentries (i.e., participants in the predictive health monitoring program) for Lawrence County are provided as a raw number (1,420) and as a percentage of the Lawrence County population (1.5%). Next, the number of sentries reporting predictive health monitoring readings for the day of the report are presented as a raw number (1,250) and as a percentage of sentries in Lawrence County (88%). Thus the significance of the data can be determined, and the integrity of the system can be monitored.

Below the aforementioned regional statistics, the actual readings for monitored individuals are presented in a three row by five column table. The three rows from top to bottom correspond to WPF readings in the fourth band 18 (indicating normal WPF), the third band 16 (indicating below normal WPF—less than 80% of Peak Best), and the second band 14 (also indicating below normal WPF—less than 60%), respectively. The five columns from left to right correspond to BMT readings in the first band 12 (normal BMT—temperatures of from 96.9° F. to 98.1° F.), the second band 14 (temperatures of from 98.1° F. to 98.5° F.), the third band 16 (temperatures of from 98.5° F. to 98.9° F.), the fourth band 18 (temperatures of from 98.9° F. to 99.3° F.), and the fifth band 20 (temperatures greater than 99.3° F.), respectively. The numbers in each cell of the matrix represent the raw number and percentage of the reporting sentries for the county that reported a WPF reading in the band corresponding to the particular row and reported a BMT reading in the band corresponding to the particular column. For example, for Lawrence County on the day of the report shown in FIG. 3, 13 sentries (1.04% of sentries reporting for Lawrence County) reported a WPF in the third band 16 (between 60% and 80%) and a BMT in the fourth band 18 (between 98.9° F. to 99.3° F.). While the foregoing example includes three bands for WPF and five bands for BMT, other arrangements using fewer or additional bands are contemplated within the scope of the invention, provided, however that at least one band corresponds to a normal range for each measured characteristic and at least one band corresponds to an abnormal range for each measured characteristic.

Figure 4:
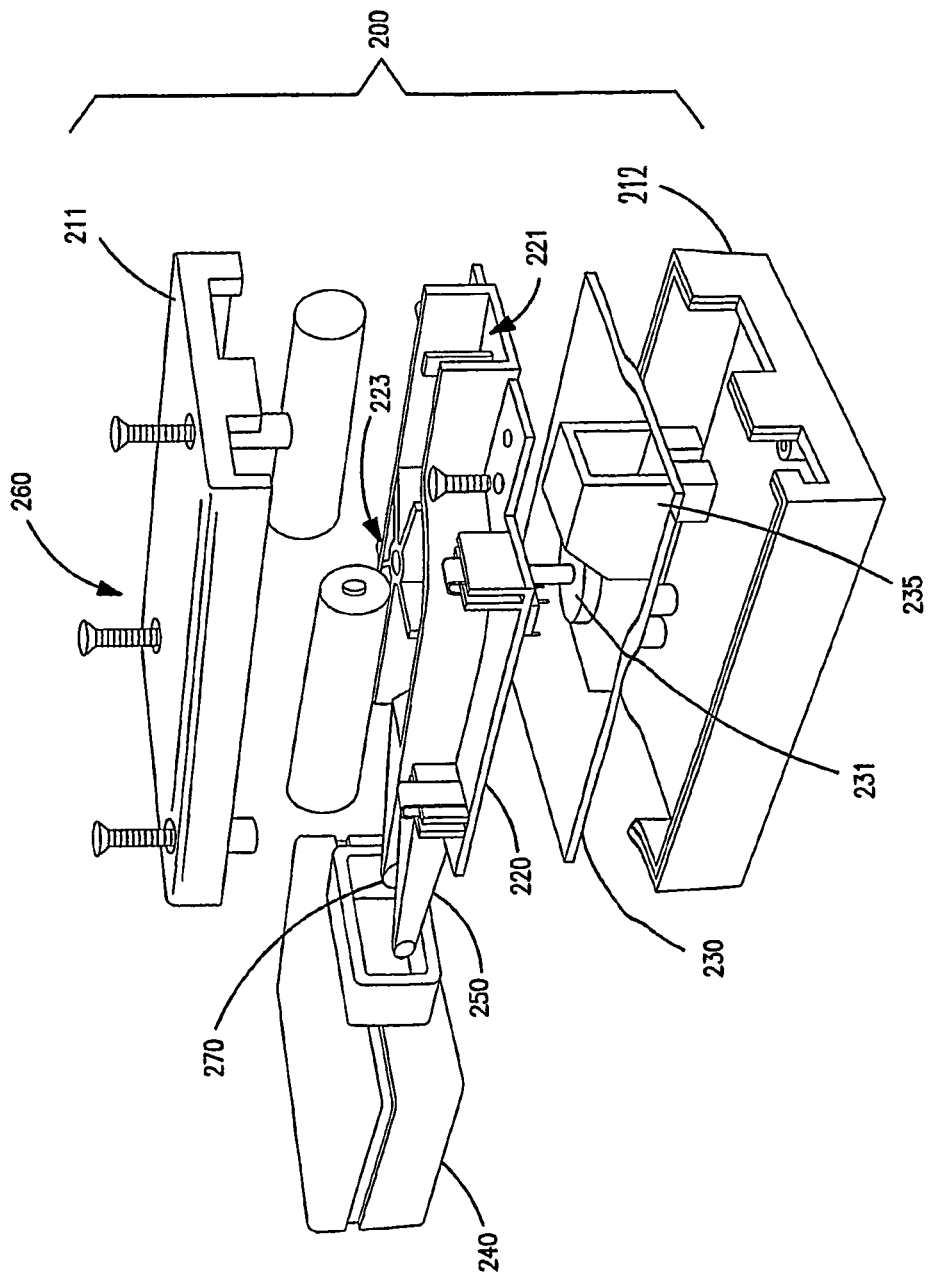
FIG. 4 shows an apparatus for reading and transmitting predictive health monitoring data according to an exemplary embodiment of the invention.

A threshold value can be set for particular cells in the table, and the cells can be highlighted when those thresholds are reached. For example, as shown in FIG. 4, the four cells in the lower right of the table for Lawrence County are highlighted, indicating a number or percentage of occurrences or events above a set threshold. As shown in FIG. 3, the health agency report 2 only tracks predictive health monitoring reading statistics for a population, and therefore individual readings are not shown, maintaining confidentiality of individual medical records.

Apparatus for Measuring WPF/BMT

It is important for effective predictive health monitoring, that the BMT and WPF be taken immediately when an individual is awakened. It is further necessary that the readings be accurately entered into the data collection and analysis program on the health monitoring computer 130. In an exemplary embodiment of the invention, an apparatus and method are provided for accurately taking and entering BMT and WPF readings. A combination peak flow meter and basal thermometer (WPF/BMT device) 200 is provided according to an exemplary embodiment of the invention. The WPF/BMT device comprises a housing 210 having an upper housing portion 211 and a lower housing portion 212, which are attached by a suitable fastening means, such as screws and/or snap geometry. A flow meter 220 is disposed between the upper and lower housing portions 211, 212, defining a fluid flow channel 221. The fluid flow channel 221 is enclosed to contain a fluid (exhalation in the present example) and may be bounded on one or more sides by one or both housing portions 211, 212. An impellor 223 is disposed in the fluid channel, such that it is rotated by the fluid that passes through the fluid channel. The impellor 223 may, for example, include a permanent magnet. The peak flow rate (PFR) may be determined, for example, by a field-effect transistor 231 that senses the rotating magnet within the impellor 223. The field-effect transistor 231 is mounted on a printed circuit board (PCB) 230 and the peak flow reading is read by counting the number of rotations of the impellor 223 per second. The information is stored digitally in a memory device on the PCB 230. A mouthpiece 240 is configured to be placed in the mouth and form a fluid tight seal during exhalation to direct exhaled fluid into the flow channel 221 to measure PFR.

A rapid electronic thermometer probe 250 is disposed in the mouthpiece 240 and electrically connected to the PCB 230 to measure basal metabolic temperature and provide a digital value to the memory device on the PCB 230. Thus, WPF and BMT can be measured simultaneously, by placing the mouthpiece 240 of the WPF/BMT device 200 into the mouth and, after BMT is acquired, forcefully exhaling.

The PCB may also have a connector 235, which readily mates with a standard phone plug, for automatic transmission of the stored digital values for WPF and BMT. Thus, digitally recorded values can be transmitted over a telephone network 111 or the Internet 121 without keying numbers or verbal communication, eliminating a significant source of data entry errors, enhancing the convenience and accuracy of the predictive monitoring system.

In an exemplary embodiment of the invention a means to detect waking heart rate (WHR), waking saliva acidity (WPh) and/or waking blood oxygen (WO2) are also incorporated in the WPF/BMT device 200. The WPF/BMT device 200 may include a detection device 260 comprising a sensing module (Sensing Module) which includes a light source of two wave lengths, such as 650 nm and 805 nm as used in pulse oximetry, a detector or multiple detectors capable of sensing the two near infrared wavelengths of light as well as infrared radiation and an electronic circuit with firmware capable of determining with relative (i.e., reading to reading) accuracy the heart rate and percentage of oxygen saturation observed by the sensing module when an individual's finger or thumb is brought in close proximity to the Sensing Module.

Also in an exemplary embodiment of the invention a second probe (WPh Probe) 270 disposed in the mouthpiece 240 and electrically connected to the PCB 230, similar to the basal thermometer probe in the exemplary embodiment, may be incorporated to (i) assist the person being monitored in accurately positioning both probes in the mouth on each side of the bottom of the tongue and (ii) provide waking saliva acidity (WPh) readings by determining the galvanic potential or electrical resistance between the metal tip of the basal thermometer probe and the metal tip of the WPh Probe 270.

Description of Operation

In an exemplary embodiment of the invention, the WPF/BMT device 200 or other discrete means to measure WPF and BMT are placed by an individual's bedside near or next to a waking device (e.g., alarm clock). Upon waking, WPF and BMT are acquired under basal conditions (and in an ideal embodiment of the invention WHR, WPh and WO2 are also acquired) by the individual or their caretaker and forwarded to the data collection and analysis program on a health monitoring computer 130 (i.e., Remote System) either automatically (as described above) or manually by any convenient means such as phone, email, or Internet website. The data forwarded may also include the individual's answers to health-related questions.

The Remote System receives the daily readings and answers to health-related questions and stores the reading values and other data using a code number or numbers to identify the data stored. If an Internet website page is used to enter the data, a page may be displayed confirming that the data was received, which page may also include immediate analytical information and recommendations based on the data submitted. The same analytical information and recommendations may be obtained from an auto-attendant if a telephone is used to enter data or from email software designed to respond in the same manner to email submissions.

Either when requested or as soon as new data is received, the Remote System will graph the individual's correlated data, i.e., WPF, BMT, etc., on a predictive health monitoring chart 1 and health agency report 2 with answers to health-related questions, and upload the predictive health monitoring chart 1 and health agency report 2, so that they may be viewed on the Internet or emailed to the individual, healthcare personnel, and/or government officials.

The foregoing illustrates some of the possibilities for practicing the invention. Many other embodiments are possible within the scope and spirit of the invention. It is, therefore, intended that the foregoing description be regarded as illustrative rather than limiting, and that the scope of the invention is given by the appended claims together with their full range of equivalents.

What is claimed is:

1. An apparatus for simultaneously measuring basal metabolic temperature, waking peak flow, plus one or more of heart rate, blood oxygen percentage and saliva acidity; the apparatus comprising:
   a fluid channel for passing exhaled fluid and having an impellor disposed therein for measuring peak volumetric flow of fluid through the fluid channel by sensing a rotating magnet within the impellor with a field-effect transistor counting the numbers of rotations per second of the impellor;
   a mouthpiece positioned in line with the fluid channel for insertion into an individual's mouth and forming a seal with the mouth and directing exhaled fluid into the fluid channel;
   a rapid thermometer probe with a metallic tip disposed in the mouthpiece for measuring basal metabolic temperature at a sublingual location when the mouthpiece is inserted into the mouth;
   a second probe with a metallic tip disposed in the mouthpiece for measuring saliva acidity at a sublingual location when the mouthpiece is inserted into the mouth; and,
   a digital memory for storing measured values for basal metabolic temperature, waking peak flow, and saliva acidity (Ph).

2. The apparatus of claim 1 further comprising a connector for transmitting the measured values to a remote location.

3. The apparatus of claim 1 further comprising a wireless means for transmitting the measured values to a remote location.

4. The apparatus of claim 1 wherein said fluid channel has at least one continuous wall extending from the mouthpiece to an exit.

5. A measuring apparatus comprising:
   a mouthpiece configured to be placed in a user's mouth and forming a fluid tight seal therewith during exhalation to direct exhaled fluid into the apparatus;
   a fluid channel extending in a plane defined by a straight path from the mouthpiece to an exit;
   an impellor disposed in the fluid channel;
   a rotating magnet coupled to the impellor;
   a field-effect transistor sensing the rotating magnet and counting the number of rotations per second of the impellor;
   a rapid thermometer probe with a metallic tip disposed in the mouthpiece and measuring basal metabolic temperature in the user's mouth; and,
   a second probe with a metallic tip disposed in the mouthpiece and measuring saliva acidity together with the first probe in the user's mouth;
   both probes being located in the mouthpiece to accurately position them in opposing lateral sublingual positions in the user's mouth.

6. The apparatus of claim 5 further comprising a memory storing measured values of basal metabolic temperature, peak flow and saliva acidity.

7. The apparatus of claim 5 further comprising an electrical connector.

8. The apparatus of claim 5 further comprising a sensing module having a light source, the sensing module being disposed on the apparatus to accommodate one of the user's fingers.

9. The apparatus of claim 8 wherein the sensing module measures heart rate.

10. The apparatus of claim 8 wherein the sensing module measures percentage of oxygen saturation in the finger.

11. The apparatus of claim 10 further comprising a memory storing measured values of heart rate and percentage of oxygen saturation.

12. The apparatus of claim 5, wherein the rapid thermometer probe and the second probe are spaced apart from each and extend through the mouth piece and for positioning on each side of a bottom of a tongue respectively.

13. The apparatus of claim 1, wherein the rapid thermometer probe and the second probe are spaced apart from each and extend through the mouth piece and positioning on each side of a bottom of a tongue respectively.

* * * * *